United States Patent [19]
Sarna

[11] Patent Number: 4,869,809
[45] Date of Patent: Sep. 26, 1989

[54] AROMATICS EXTRACTION PROCESS CONTROL

[75] Inventor: Michael E. Sarna, Mt. Prospect, Ill.

[73] Assignee: UOP, Des Plaines, Ill.

[21] Appl. No.: 192,018

[22] Filed: May 9, 1988

[51] Int. Cl.$^4$ ............................................. G06G 7/58
[52] U.S. Cl. .................... 208/311; 208/321;
208/DIG. 1; 585/804; 585/807
[58] Field of Search ................. 208/311, 321, DIG. 1;
585/804, 807, 808

[56] References Cited

U.S. PATENT DOCUMENTS

| | | | |
|---|---|---|---|
| 2,911,361 | 11/1959 | Kleiss | 208/311 |
| 3,546,107 | 12/1970 | Brown et al. | 208/DIG. 1 |
| 3,666,931 | 5/1972 | Woodle | 208/311 |
| 3,718,809 | 2/1973 | Woodle | 208/311 |
| 4,212,070 | 7/1980 | Sequeira, Jr. et al. | 208/DIG. 1 |
| 4,224,673 | 9/1980 | Sequeira, Jr. et al. | 208/311 X |
| 4,224,674 | 9/1980 | Sequeira, Jr. et al. | 208/311 X |
| 4,545,894 | 10/1985 | Stewart et al. | 208/311 |

OTHER PUBLICATIONS

Advanced Process Control Handbook III, "Hydrocarbon Processing", Mar. 1988, pp. 60–64.
Advanced Process Control Handbook III, "Hydrocarbon Processing", Mar. 1987, pp. 63–64.

Primary Examiner—Glenn Caldarola
Attorney, Agent, or Firm—Thomas K. McBride; John F. Spears, Jr.

[57] ABSTRACT

A process for separation of aromatic and nonaromatic hydrocarbons by solvent extraction is improved by incorporating control methods which optimize utility costs while maintaining desired product purities.

10 Claims, 2 Drawing Sheets

AROMATICS EXTRACTION PROCESS CONTROL

The invention concerns improvements in a process extraction of aromatic hydrocarbons from a feedstock containing both aromatic and non-aromatic hydrocarbons. Particularly, the invention relates to those aromatics extraction processes which employ sulfolane, or similar solvents such as polyglycols, dimethyl sulfoxide, Nformylmorpholine and the like.

PRIOR ART

Aromatics extraction using sulfolane or similar solvents is well known in the art. Many patents disclose the process generally and variations intended to improve efficiency. The process may be generally described as follows.

A feedstock containing up to about 60-80 vol. percent aromatics, particularly benzene, toluene, and xylenes, is countercurrently extracted with a stream of lean solvent and split into an aromatic extract stream and a non-aromatic raffinate stream. The aromatics are separated from the solvent which then recirculates to extract more aromatics. When the process is properly operated, only negligible amounts of the solvent are lost. Water also recirculates within the process with some being lost with the aromatics produced. The water is used to wash residual solvent from the raffinate and to strip (as steam) aromatics from the solvent.

The operator of such a process wants to separate the aromatics in the feedstock efficiently and certain guidelines may be established. First, the separation of aromatics from nonaromatics should be sufficient to meet but not exceed the desired product purities since making unnecessarily high-purity aromatics will increase utility costs. Internal recycle streams should be minimized also to hold utility costs down while producing aromatics of the desired purity. Losses of solvent should be minimized but consistent with the overall objective of optimizing the costs of the separation.

From this brief description, it can be seen that achieving efficient recovery of aromatics involves a number of factors which are interrelated and that a unified procedure for achieving the goals is required. Such processes are presently operated to produce high-purity aromatics, but not as efficiently as possible. The present invention is directed toward increased efficiency in operation of such processes.

Control techniques for aromatics extraction processes have been offered by several suppliers as is shown in the brief description given in *Hydrocarbon Processing*, March 1988, pages 60-64, and *Hydrocarbon Processing*, March 1987, pages 63-64. However, the methods suggested differ in important respects from the process to be described below.

SUMMARY OF THE INVENTION

A process for separating aromatic hydrocarbons from a feedstock mixture containing both aromatic and non-aromatic hydrocarbons which employs countercurrent extraction using a solvent, e.g. sulfolane and the like is improved by:

(a) controlling the concentration of hydrocarbons in the aromatics-rich solvent leaving the extractor;

(b) maintaining the pressure of the stripping column used to separate nonaromatics from the aromatics-rich solvent at the maximum value permitted by thermal degradation of the solvent;

(c) controlling the amount of the residual hydrocarbons recycled from the stripping column by the quantity of the aromatics product;

(d) controlling the amount of stripping steam used in separating aromatics product from the rich solvent by the amount of lean solvent recycled to the extractor; and, (e) maintaining a predetermined concentration of solvent in the aromatics product. These objectives may be accomplished by various means discussed in detail hereinafter.

DESCRIPTION OF THE PREFERRED EMBODIMENTS

The invention is best understood by first considering the separation of a feedstock containing a significant fraction of aromatic compounds, typically up 60-80 volume percent. The aromatic and nonaromatic hydrocarbons in the feedstock are separated almost completely with high purities. A feature of this process is that the solvent which is used for extraction is very efficient and is retained almost entirely within the separation system and requires very little makeup of fresh solvent, although some must be purged and purified before reuse. Typically, the process is operated using sulfolane as a solvent, however, other solvents of a similar nature may be used such as polyglycols, dimethyl sulfoxide, N-formyl morpholine and the like.

Figure 1:
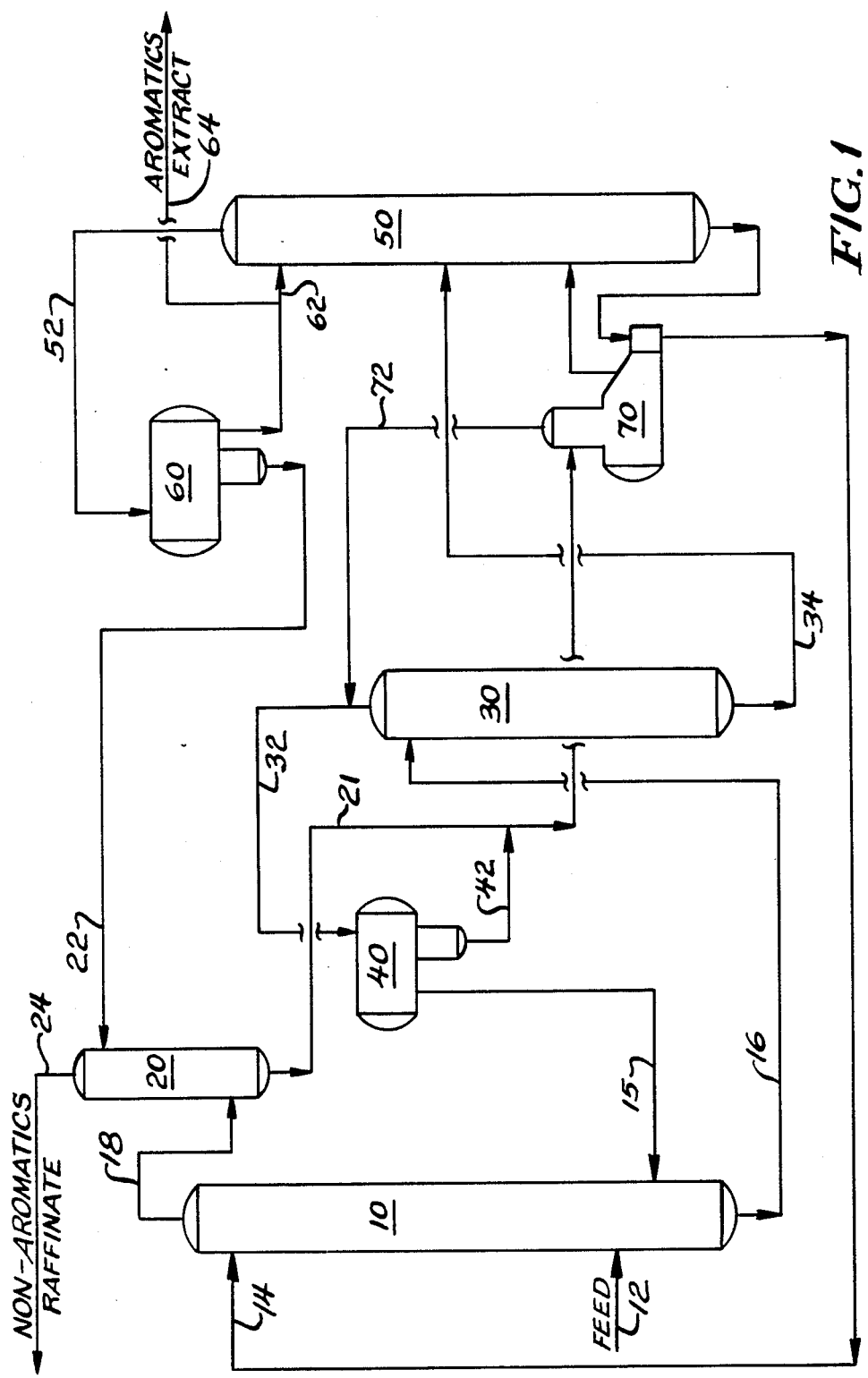
FIG. 1 is a simplifed flowsheet of a typical aromatics extraction process of the invention.

The process is illustrated in a simplified form in FIG. 1 in which only the major vessels used in the process are shown. It is to be understood that in any detailed flow sheet many more pieces of equipment and instrumentation will be necessary. As seen in FIG. 1, the feedstock 12 is supplied to the bottom of an extraction column 10 which may be a rotating disc contactor, or a column using trays, packing or the like. A lean solvent stream 14 is passed countercurrently to the feed. The solvent stream will consist primarily of the extracting solvent, such as sulfolane, but including also minor amounts of water and any residual hydrocarbons which are not removed in the recovery column 50. The solvent enters the top of the extraction column 10 and passes downward while contacting the feedstream so that at the bottom of column 10 what was previously termed a lean solvent has become aromatics-rich solvent 16. The hydrocarbon concentration in the solvent may be quite substantial, and typically is in the range of 18 to 45 volume percent. It is one of the features of the present invention to optimize the amount of hydrocarbons picked up by the solvent.

The feedstream gives up its aromatics as it passes upward against the downflowing solvent and at the top of the column substantially only nonaromatic compounds remain. However, they will contain a small amount of solvent which should be recovered. Consequently, the nonaromatic stream 18 is scrubbed in raffinate water wash column 20 countercurrently against a circulating stream of water 22 which is described in more detail later. The scrubbed product stream 24 is termed the raffinate. It comprises substantially all of the nonaromatic compounds introduced with the feed with very little residual solvent, say 5 ppm, and substantially no aromatic compounds when the process is operated efficiently.

Another stream 15 which enters the extraction column 10 and which will be discussed in more detail later enters near the bottom of the extraction column 10. It is a recirculating stream which contains a substantial fraction of aromatics but more importantly, contains nonaromatic compounds which are purged from the aromatics-rich solvent in stripper 30 in order to avoid contaminating the aromatics product 64. This stream 15 is introduced toward the bottom of column 10 where it displaces the heavier nonaromatic components so that they pass up the column and out with the raffinate stream 24.

The aromatics-rich solvent 16 is passed to a reboiled stripping column 30 where the minor amounts of nonaromatic compounds which are present in the aromatics-rich extract are rejected. Stripping column 30 is important in maintaining the purity of the aromatics product 64, which may easily be above 99 percent aromatics. In order to remove the minor amounts of nonaromatics, it is necessary to remove a portion of the lighter aromatics, particularly benzene, overhead as well. The overhead vapor stream 32 from stripping column 30 is cooled and condensed and phase separated in vessel 40. The hydrocarbons are recycled as stream 15 to the extraction column 10 as previously mentioned. Since water is present in the solvent as it enters the extractor, water also appears in the overhead vapor 32 of the stripping column 30 and when condensed separates from the hydrocarbons and returned via stream 42 to water-handling facilities to be discussed later.

The aromatics-rich solvent leaving as stream 34 from the bottom of the stripping column 30 now is substantially free of nonaromatic compounds and is ready for separation of the aromatics from the solvent which takes place by distillation in recovery column 50. Column 50 is reboiled to generate stripping vapor and the overhead vapor 52 is condensed. A portion of the condensate is drawn off as the aromatics extract product 64. A portion of the hydrocarbon condensate is returned as reflux 62 to the column to maintain the desired degree of separation of aromatics from solvent. Stripping steam is introduced toward the bottom of the column 50 in order to reduce the solubility of hydrocarbons in the solvent and consequently to lower their concentration in the lean solvent which is to be reused for extraction. The steam is generated from water obtained from two sources, the first being the water leaving the raffinate water wash column 20, and the second water condensed and separated from the stripper overhead. These two streams (21 and 42) will contain a minor amount of hydrocarbons. In order to avoid contamination of the solvent, these water streams are stripped in water stripping column 70 to provide an essentially hydrocarbon-free water for use as stripping steam in the recovery column 50. The hydrocarbons recovered are then recycled to the extractor column 10 by way of the stripper overhead system. The overhead vapor 52 from recovery column 50 is cooled and condensed. A hydrocarbon portion is separated as product and another portion recycled as reflux to the recovery column as previously mentioned. In addition, water present in overhead vapor 52 is condensed to liquid water which is separated in vessel 60 and then returned to the raffinate water wash column 20 via stream 22 as a means of removing trace solvent from the raffinate as previously explained.

It can be seen that the overall process is one in which a mixed hydrocarbon feedstock (12) containing significant amount of aromatic hydrocarbons is split into a nonaromatic raffinate (24) and an aromatic hydrocarbon extract (64). The solvent circulates from the extraction column 10 to the stripping column 30, then to the recovery column 50, and back to extraction column 10 again. Since sulfolane is a particularly stable material under the conditions in which it is used in this process only a minor purge is required in order to rid the stream of any buildup of heavy compounds or degradation products. This is not shown in the flowsheet since it is only incidental to the process of the invention. Water also circulates continuously through the process, being used to wash the raffinate free of solvent in column 20 and to supply stripping vapor for use in recovery column 50 to remove hydrocarbons from the solvent before it is reused in extraction column 10. It will be evident to one skilled in the art that the process is an energy-intensive one since the separations involve vaporization and condensation of recycle stream 15, recovery column reflux and the extract product 64 as well as the water which is continuously recirculated. As might be expected, the greater the purity of the extract product, the larger the utility cost. Since the purity of the extract product is determined by its anticipated use, it is clear that the most efficiently operated process would be one which meets but does not significantly exceed the desired product composition. It is, however, typical of commercial operations that the equipment is operated conservatively in order to avoid off-specification extract product which may occur when feed composition changes occur or upsets occur in the operation of the equipment. Consequently, it is the objective of the inventor to provide a process which can be operated most efficiently and assure an extract product which meets specifications.

Extensive experience, including both actual operation and study of the process, has led to the discovery that there are certain critical aspects of the process operation which must be observed if optimum separation efficiency is to be obtained. One of the most important variables in the process is the concentration or loading of the hydrocarbons in the solvent at the bottom of the extraction column 10. It is evident that if a large amount of solvent is passed through the column that the removal of aromatics from the feedstock will be quite complete since the solvent is highly selective for aromatic hydrocarbons when the loading is low. The solvent will also have reduced capacity for nonaromatic hydrocarbons. However, the efficiency of separation will suffer since the aromatic hydrocarbons will require more stripping steam to free them from the increased solvent. In addition, the cost of circulating a large amount of solvent will make it undesirable. Conversely, if only a very small amount of solvent is circulated relative to the feed composition, it is clear that aromatic compounds may well be lost to the raffinate providing a pure product but achieving a less than complete recovery. In addition if the solvent circulation rate is too low, larger amounts of nonaromatics will be absorbed as the selectivity falls off and these nonaromatics will have to be vaporized, condensed, and recycled to the extraction column causing a loss in separation efficiency. It is also possible to obtain such large concentrations of aromatics in the solvent that the phase separation which is essential for effective countercurrent extraction, may no longer occur. Consequently, at that point feedstock would be swept into the solvent and substantial amounts of nonaromatic materials would pass to the stripper. Not being designed for such an extreme situation, nonaromatic materials would inevitably find their way into the extract. It is evident then that attention must be paid to providing the optimum circulation of solvent relative to the feed rate and concentration of aromatics. It should be understood that since the purity of the product will ordinarily be greater than 99%, large variations in solvent circulation will not ordinarily be observed in day-to-day operation of such an extraction process. However, providing the optimum circulation rate of the solvent has been found to have an important effect on the utility cost of separating aromatics. The difference in the cost, for example, between a 99% pure aromatic extract and a 99.5% product is quite large. Consequently, the concentration of hydrocarbons in the aromatics-rich solvent at the bottom of the extraction column is controlled to an optimum value.

Figure 2:
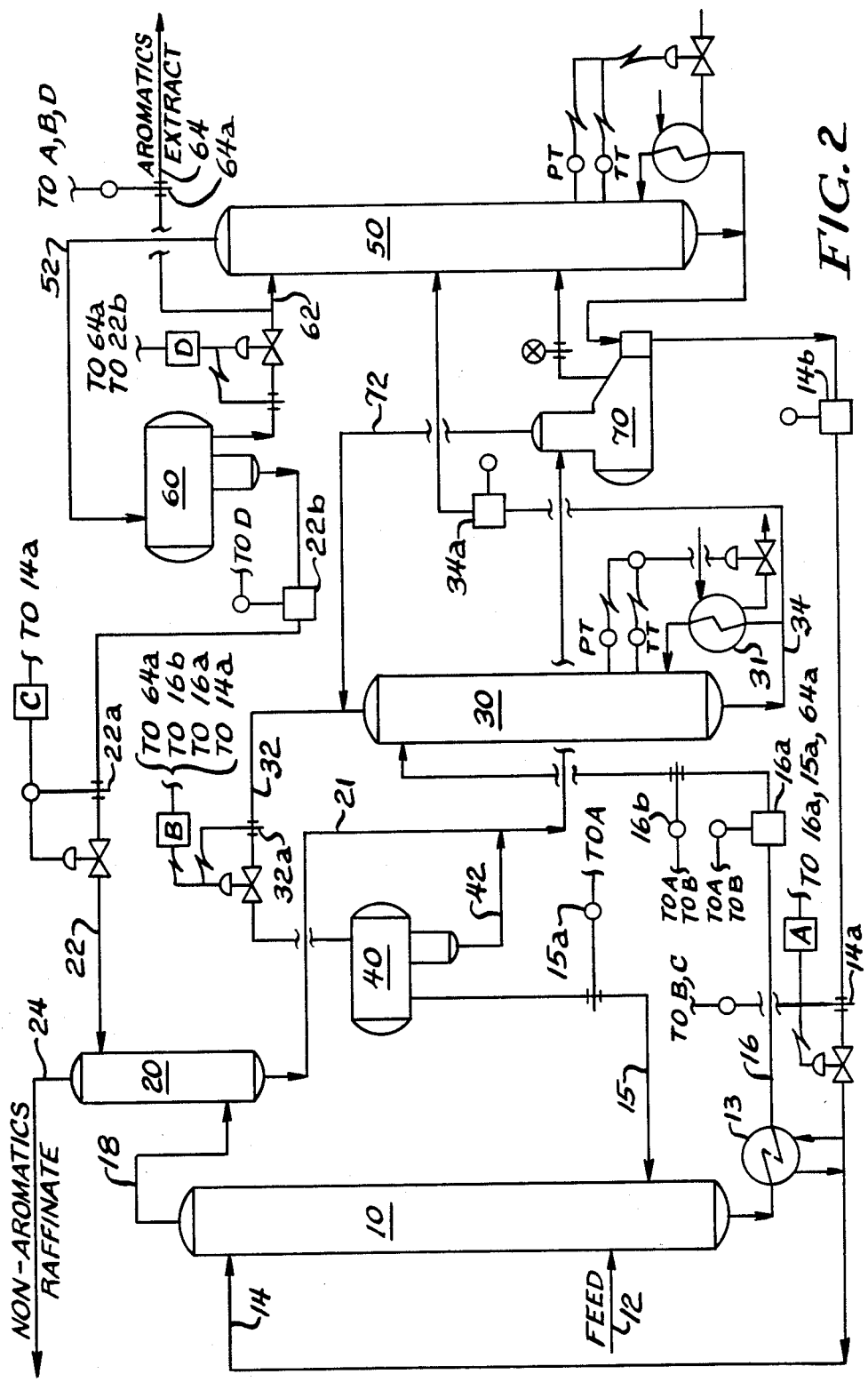
FIG. 2 is the flowsheet of FIG. 1 with control methods according to the invention added.

In order to obtain the optimum hydrocarbon loading in the aromatics-rich extract, the circulation rate of solvent to the extraction column may be controlled in at least three ways which are illustrated in FIG. 2. The most direct method of adjusting the circulation of lean solvent would be to provide an onstream analyzer 16a on stream 16 from the bottom of the extraction column to determine the total hydrocarbon loading of the rich solvent. The residual hydrocarbons in the lean solvent could be measured by an onstream analyzer 14b or by laboratory methods. By knowing the desired loading for a given feed composition and product purity, it would be possible to directly control the circulation of solvent to accommodate changes in the operation. This would be true regardless of the nature of the change, since the composition and flowrate of the feed 12 or the recycle stream 15 or the lean solvent 14 all will affect the loading of the aromatics-rich solvent in stream 16.

An indirect method which may also be used would measure the flow of the product extract 64a and the flow rate of the recycle stream 15a the sum of which divided by the rich solvent flow would equal the hydrocarbon loading of the aromatics-rich solvent at the bottom of the extraction column. By combining the two flow rates, the rate of the lean solvent to the column could be adjusted via flow controller 14a to provide the desired loading of the rich solvent.

Another indirect method which may be used is to measure the flow of the aromatics-rich solvent 16b and the flow of the lean solvent to the column 14a, the difference being the hydrocarbon which is absorbed by the solvent in the extraction column. Then the lean solvent rate could be set to provide for the optimum loading necessary to provide the desired extract purity, that is the optimum ratio of the aromatics-rich solvent to the lean solvent.

It is assumed in the foregoing discussion that prior knowledge enables one to determine the optimum setting for the hydrocarbon loading of the rich solvent. In the absence of this information, it could be obtained by observation of the effect on extract purity when the lean solvent circulation rate is reduced assuming that he feed enters at a constant rate and composition and all of the variables remain the same.

As will be evident from the previous discussion, the hydrocarbon loading of the aromatics-rich solvent leaving the bottom of the extraction column will have a substantial effect on the performance of the stripping column 30. Its purpose is to remove the relatively small amount of nonaromatics which is present in the rich solvent. Removing nonaromatics requires vaporization of a significant amount of the lighter aromatics compounds, particularly benzene, in the stripping column. As shown in the diagram, rich solvent is heated in exchanger 13 by the loan solvent and then passes into the top portion of the stripping column 30 at a somewhat lower pressure and higher temperature than had existed in the extraction column. Consequently, some of the rich solvent flashes and additional vaporization occurs as a result of heat input from reboiler 31 at the bottom of the stripping column. No direct reflux is used as in the typical fractionation column and the feed composition serves in effect as reflux. The amount of hydrocarbon which passes overhead via stream 32 in the stripping column thus is affected by the degree of loading of the rich solvent, the temperature at which the rich solvent enters the stripping column, and the heat input from the reboiler. Also affecting the amount of vapor formed is the pressure in the stripping column, which affects the degree of vaporization of the incoming feed and temperatures throughout the column, particularly the temperature at the bottom of the column. Depending upon the solvent used and the composition at the bottom of stripping column 34, there will be found a maximum temperature above which degradation of the solvent quality will become significant making it necessary to purge and reclaim greater amounts of solvent. Degradation of the solvent also leads to fouling and corrosion problems. Obviously, this is not desirable and so this maximum temperature usually determines the limiting temperature at the bottom of column 30, unless some other consideration requires a lower value. It has been found that in order to improve the stripping efficiency flashing of the rich incoming solvent should be suppressed. This means that the pressure of column 30 should be increased insofar as it does not cause temperature at the bottom to exceed the maximum allowable temperature. The inventor proposes that control of the stripping column should be carried out as indicated in the figure and that the maximum allowable temperature at the bottom of the stripping column should be achieved simultaneously with the maximum allowable pressure in the stripping column. Consequently the pressure would be allowed to determine the amount of stripping vapor which is provided by reboiler 31 but limited when the maximum temperature at the bottom of the column is achieved. By operating the stripping column at its optimum point, the control of the amount of nonaromatic material passing to the extract product can be adjusted to its optimum level and the degree of recycle to the extraction column can be optimized.

As previously discussed, it is important in controlling extract purity that all of the nonaromatics in the rich extract (16) must be returned to the extraction column from the overhead of the stripping column. On the other hand, if a quantity of material is vaporized, condensed, and recycled to the extraction column beyond that necessary to maintain extract purity, a substantial loss of efficiency is involved since the recirculating material must be vaporized, condensed and recycled, thereby incurring substantial utility costs. Consequently, it is desirable to control the recycle hydrocarbon stream (15) to the minimum consistent with meeting aromatics purity. Obviously since this is the primary control of extract quality, a direct measurement of the purity of the extract could be used to control the rate at which hydrocarbons are returned to the extraction column via stream 15. This appears to be suggested in the *Hydrocarbon Processing* publications previously mentioned. However, since the purity of the extract product is ordinarily quite high, the accuracy of such control systems is questionable. Consequently the inventor proposes several means which provide for adjustment of product quality and more compatible with the realities of the day-to-day operation.

It can be seen from FIG. 2 that if the vapor flow (in stream 32) from the top of stripping column 30 is reduced, then the net effect will be to raise the pressure on stripping column 30 which will then be reflected in a reduction in the amount of stripping vapor provided and in the amount of hydrocarbon loading of the rich solvent. If the loading of the rich solvent is measured directly by an onstream analyzer 16a, then it may used to directly reset flow controller 32a for the recirculation of hydrocarbon to the extractor.

Another method measures the rate at which the lean solvent is entering the extraction column (14a) and the rate at which the rich solvent leaves the extraction column (16b), the difference divided by the lean solvent being equal to the hydrocarbon loading as discussed above. This difference may then be used to set the amount of hydrocarbon recycle rate (32a) which is desired.

A third method of controlling the recycle of hydrocarbons (via stream 15) to the extraction column is to adjust flow controller 32a by the flow of aromatics extract measured by flow of the aromatics extract product 64. This will assure that changes in the amount of aromatics supplied in the feed stream and/or extract will be reflected in a change in the recycle from the stripping column. Fine adjustment can be accomplished by measuring the amount of nonaromatics in the product. An onstream analyzer can also be provided for measuring the amount of nonaromatics in the bottoms of the stripper (34a). This value could be used to determine the correct ratio of the hydrocarbon recycle to the extract product. Laboratory analysis could also be used.

As explained earlier, water is continually circulating through the process system. It has two principal purposes: first, it removes residual solvent from the raffinate stream in the water wash column; and, second, it strips (as steam) aromatic hydrocarbons from the solvent in the recovery column 50. The residual water in the lean solvent has an impact on its ability to extract aromatics and consequently it is an important factor to be considered in determining the optimum operation of the process. If the water level in the solvent becomes too high, then its ability to extract hydrocarbons is reduced and consequently more solvent must be recirculated in order to extract the amount of hydrocarbons. At the same time, if the water level in the solvent is high, the amount of aromatics lost to the raffinate will increase. Consequently, the water level in the lean solvent stream should be controlled. In addition, a certain amount of water must be vaporized in recovery column 50 in order to provide water for raffinate water wash column 20, since water which leaves the recovery column dissolved in the solvent is not available for use in the water wash column. The water flow to the water wash column (22e) can be adjusted to maintain a constant water-to-lean solvent flow rate (14a) as is suggested in the *Hydrocarbon Processing* publications previously mentioned. This minimizes the amount of water which must be vaporized in recovery column 50 to that necessary to control the amount of aromatic compounds found in the recirculating lean solvent. The aromatics may be measured and the stripping steam adjusted as required.

The purpose of the recovery column 50 is to separate the solvent from the aromatics extract. An extremely pure aromatics product is normally required. Consequently, an extract should not contain significant quantities of the solvent and of course solvent losses would be expensive. This can be accomplished by adjusting the reflux to product ratio in a conventional fashion. However excessive reflux rates involve substantially increasing utility costs since the reflux material must be vaporized in the reboiler 52, condensed in the overhead equipment, and returned to the column via stream 62. Consequently, only the degree of reflux required in order to achieve the desired separation should be used. While a direct measurement of the amount of solvent in the extract product could be used to determine the change in the set point for the reflux rate, it is desirable according to the invention to measure by gas chromatography or other means the amount of solvent (22b) in water stream 22 which leaves condensate drum 60 and using that measurement as an indication of the amount of solvent which is found in the extract stream. This has the advantage of avoiding measurement of low levels of solvent in the presence of aromatics which has been found unreliable. When the water is used as an indicator of the amount of solvent present, these measurements can be made directly by gas chromatography on the water stream without any pretreatment being required. Using such a control scheme permits the extract purity to be maintained while at the same time avoiding excessive losses of the solvent to the product stream.

When the control schemes outlined above are employed, the extraction process can be operated in a highly desirable manner. The feed may be separated into an extract having the required, but not excessive, purity while at the same time losses of solvent to the raffinate or to the extract are minimized. The utility costs are optimized, thus saving the operator substantial costs and reducing the need to operate in a conservative manner to avoid upsets which could degrade product quality.

What is claimed is:

1. A process for separating aromatic hydrocarbons from a feedstock mixture containing both aromatic and on-aromatic hydrocarbons comprising:
   countercurrent extraction of said feedstock with an aromatics-lean solvent stream to produce a raffinate stream containing substantially all of the non-aromatic hydrocarbons and an aromatics-rich solvent stream,
   separation of residual non-aromatic hydrocarbons from the aromatics-rich solvent in a stripping column and recycling said residual hydrocarbons to the extraction step;
   recovery of the aromatic hydrocarbons from the solvent to produce an extract product containing substantially all of the aromatics in the feedstock and a lean solvent stream which is returned to the extraction step, wherein the improvement comprises maintaining the total concentration of hydrocarbons in the aromatics-rich solvent stream at a set level between 18 and 45 vol. percent by:
   (a) measuring the extract product rate;
   (b) measuring the recycle rate of residual non-aromatic hydrocarbons to the extraction step; and, (c) controlling the flow rate of said lean solvent stream to obtain a set ratio of the sum of said extract product rate of (a) plus said recycle rate of residual non-aromatic hydrocarbons to the extraction step to the flow rate of said lean solvent stream.

2. The process of claim 1 wherein the solvent comprises sulfolane.

3. A process for separating aromatic hydrocarbons from a feedstock mixture containing both aromatic and on-aromatic hydrocarbons comprising:

countercurrent extraction of said feedstock with an aromatics-lean solvent stream to produce a raffinate stream containing substantially all of the non-aromatic hydrocarbons and an aromatics-rich solvent stream, separation of residual non-aromatic hydrocarbons from the aromatics-rich solvent in a stripping column and recycling said residual hydrocarbons to the extraction step;

recovery of the aromatic hydrocarbons from the solvent to produce an extract product containing substantially all of the aromatics in the feedstock and a lean solvent stream which is returned to the extraction step, wherein the improvement comprises controlling the vapor flow at the top of the stripping column and maintaining the extract product purity above 99 mole % by:

(a) measuring the extract product rate;
(b) measuring the recycle rate of residual hydrocarbons to the extraction step; and,
(c) adjusting said recycle rate of residual hydrocarbons to the extraction step to obtain a set ratio of said recycle rate to said extract product rate of (a).

4. The process of claim 3 wherein the solvent is sulfolane.

5. A process for separating aromatic hydrocarbons from a feedstock mixture containing both aromatic and non-aromatic hydrocarbons comprising:

countercurrent extraction of said feedstock with an aromatics-lean solvent stream to produce a raffinate stream containing substantially all of the non-aromatic hydrocarbons and an aromatics-rich solvent stream, separation of residual non-aromatic hydrocarbons from the aromatics-rich solvent in a stripping column and recycling said residual hydrocarbons to the extraction step;

recovery of the aromatic hydrocarbons from the solvent to produce an extract product containing substantially all of the aromatics in the feedstock and a lean solvent stream which is returned to the extraction step, wherein the improvement comprise controlling the vapor flow at the top of the stripping column and maintaining the extract product purity above 99 mole % by:

(a) measuring the flow rate of lean solvent to the extraction step;
(b) measuring the flow rate of aromatics-rich solvent from the extraction step;
(c) measuring the recycle rate of residual hydrocarbons to the extraction step; and
(d) adjusting said recycle rate of of residual hydrocarbons to said extraction step to obtain a set ratio of said recycle rate to the difference between the flow rate of said lean solvent to the extraction step and the flow rate of said aromatics-rich solvent from the extraction step.

6. The process of claim 5 wherein the solvent is sulfolane.

7. A process for separating aromatic hydrocarbons from a feedstock mixture containing both aromatic and non-aromatic hydrocarbons comprising:

countercurrent extraction of said feedstock with an aromatics-lean solvent stream to produce a raffinate stream containing substantially all of the non-aromatic hydrocarbons and an aromatics-rich solvent stream, separation of residual non-aromatic hydrocarbons from the aromatics-rich solvent in a stripping column and recycling said residual hydrocarbons to the extraction step;

recovery of the aromatic hydrocarbons from the solvent to produce an extract product containing substantially all of the aromatics in the feedstock and a lean solvent stream which is returned to the extraction step, wherein the improvement comprises controlling the vapor flow rate at the top of the stripping column and maintaining the extract product purity above 99 mole % by:

(a) measuring the flow rate of the aromatics-rich solvent stream from the extraction step;
(b) measuring the hydrocarbon content of the aromatics-rich solvent stream from the extraction step;
(c) measuring the recycle rate of said residual hydrocarbons to the extraction step; and,
(d) adjusting said recycle rate of residual hydrocarbons to the extraction step to provide a set ratio of aid recycle rate to the product of the flow rate of the aromatics-rich solvent stream and the hydrocarbon content of the aromatics-rich solvent stream.

8. The process of claim 7 wherein the solvent is sulfolane.

9. A process for separating aromatic hydrocarbons from a feedstock mixture containing both aromatic and non-aromatic hydrocarbons comprising:

countercurrent extraction of said feedstock with an aromatics-lean solvent stream to produce a raffinate stream containing substantially all of the non-aromatic hydrocarbons and an aromatics-rich solvent stream, separation of residual non-aromatic hydrocarbons from the aromatics-rich solvent in a stripping column and recycling said residual hydrocarbons to the extraction step;

recovery of the aromatic hydrocarbons from the solvent to produce an extract product containing substantially all of the aromatics in the feedstock and a lean solvent stream which is recycled to the extraction step, wherein the improvement comprises maintaining the total concentration of hydrocarbons in the aromatics-rich solvent stream at a set level between 18 and 45 vol. percent by:

(a) measuring the hydrocarbon content of said aromatics-rich solvent stream; and
(b) controlling the lean solvent stream recycle rate to the extraction step to maintain a set hydrocarbon content of said aromatics-rich solvent stream.

10. The process of claim 9 wherein the solvent is sulfolane.

* * * * *